(12) United States Patent
Solar et al.

(10) Patent No.: US 8,535,242 B2
(45) Date of Patent: Sep. 17, 2013

(54) METHOD OF MANUFACTURING A GUIDEWIRE WITH AN EXTRUSION JACKET

(75) Inventors: Matthew Solar, Indialantic, FL (US); Richard Acevedo, Hollywood, FL (US); Eric Welch, Miramar, FL (US); Scott Jones, Pembroke Pines, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1202 days.

(21) Appl. No.: 11/826,766

(22) Filed: Jul. 18, 2007

(65) Prior Publication Data

US 2008/0173391 A1   Jul. 24, 2008

Related U.S. Application Data

(60) Continuation of application No. 10/431,378, filed on May 8, 2003, now Pat. No. 7,670,526, which is a continuation of application No. 10/376,324, filed on Mar. 3, 2003, now Pat. No. 7,241,406, which is a division of application No. 09/749,381, filed on Dec. 28, 2000, now Pat. No. 6,554,942.

(51) Int. Cl.
| | |
|---|---|
| *A61M 25/00* | (2006.01) |
| *A61M 5/00* | (2006.01) |
| *B28B 3/20* | (2006.01) |
| *B29C 47/00* | (2006.01) |
| *B29C 47/78* | (2006.01) |

(52) U.S. Cl.
USPC ............... 600/585; 264/176.1; 264/177.1; 264/211.24

(58) Field of Classification Search
USPC ........... 600/585; 428/600; 264/176.1, 177.1, 264/211.24
See application file for complete search history.

(56) References Cited

U.S. PATENT DOCUMENTS

| | | | |
|---|---|---|---|
| 3,404,203 A | 10/1968 | Donald | |
| 3,876,743 A | 4/1975 | Soderlund et al. | |
| 4,354,989 A | 10/1982 | Beach | |
| 4,451,306 A | 5/1984 | Verne | |
| 4,676,249 A * | 6/1987 | Arenas et al. | 600/434 |
| 4,790,970 A | 12/1988 | Kurth et al. | |
| 4,796,642 A * | 1/1989 | Harris | 600/585 |
| 4,854,330 A * | 8/1989 | Evans et al. | 600/585 |
| 4,934,380 A | 6/1990 | de Toledo | |
| 4,951,686 A | 8/1990 | Herlitze | |
| 4,991,602 A | 2/1991 | Amplatz et al. | |
| 5,067,489 A * | 11/1991 | Lind | 600/585 |
| 5,230,348 A * | 7/1993 | Ishibe et al. | 600/585 |
| 5,238,004 A | 8/1993 | Sahatjian et al. | |
| 5,248,305 A | 9/1993 | Zdrahala | |
| 5,275,814 A | 1/1994 | Wojdani | |
| 5,385,152 A | 1/1995 | Abele et al. | |
| D363,544 S | 10/1995 | Rowland et al. | |

(Continued)

*Primary Examiner* — Rene Towa
*Assistant Examiner* — Adam Eiseman
(74) *Attorney, Agent, or Firm* — Seager, Tufte & Wickhem LLC (57) ABSTRACT

A method of manufacturing a guidewire having a discrete length. The method includes the steps of feeding a first end of a corewire into an extrusion device, gripping the first end of the corewire with a gripping apparatus, and extruding a first extrusion material onto an outer surface of the corewire while the gripping apparatus pulls the corewire through the extrusion device to form an extrusion jacket on the outer surface of the corewire. The corewire has a predetermined length corresponding to a length of the guidewire.

11 Claims, 11 Drawing Sheets

(56) References Cited

U.S. PATENT DOCUMENTS

| | | |
|---|---|---|
| D363,776 S | 10/1995 | Rowland et al. |
| 5,497,786 A * | 3/1996 | Urick .................... 600/585 |
| 5,546,948 A | 8/1996 | Hamm et al. |
| 5,599,492 A | 2/1997 | Engelson |
| 5,614,136 A | 3/1997 | Pepin et al. |
| 5,639,409 A | 6/1997 | van Muiden |
| 5,673,707 A | 10/1997 | Chandrasekaran |
| 5,725,814 A | 3/1998 | Harris |
| 5,772,609 A | 6/1998 | Nguyen et al. |
| 5,788,654 A * | 8/1998 | Schwager ................. 600/585 |
| 5,836,893 A * | 11/1998 | Urick ....................... 600/585 |
| 5,891,055 A * | 4/1999 | Sauter ...................... 600/585 |
| 5,916,178 A * | 6/1999 | Noone et al. ............. 600/585 |
| 5,951,494 A | 9/1999 | Wang et al. |
| 5,957,865 A * | 9/1999 | Backman et al. ......... 600/585 |
| 6,033,720 A | 3/2000 | Stoltze et al. |
| 6,042,553 A * | 3/2000 | Solar et al. ............... 600/585 |
| 6,165,166 A | 12/2000 | Samuelson et al. |
| 6,371,929 B1 | 4/2002 | Steele |
| 6,402,706 B2 * | 6/2002 | Richardson et al. ...... 600/585 |
| 6,554,942 B2 | 4/2003 | Solar et al. |
| 6,776,945 B2 | 8/2004 | Chin et al. |
| 2001/0043998 A1 | 11/2001 | Chen et al. |
| 2004/0064130 A1 | 4/2004 | Carter |
| 2004/0167436 A1 * | 8/2004 | Reynolds et al. ......... 600/585 |
| 2010/0159117 A1 * | 6/2010 | Griffin et al. ............ 427/2.11 |

* cited by examiner

METHOD OF MANUFACTURING A GUIDEWIRE WITH AN EXTRUSION JACKET

This is a continuation of application Ser. No. 10/431,378, filed May 8, 2003 now U.S. Pat. No. 7,670,526, which is a continuation of application Ser. No. 10/376,324, filed Mar. 3, 2003, now U.S. Pat. No. 7,241,406 issued Jul. 10, 2007, which is a division of application Ser. No. 09/749,381 filed Dec. 28, 2000, now U.S. Pat. No. 6,554,942 issued Apr. 29, 2003, all of which are incorporated herein by reference.

BACKGROUND OF THE INVENTION

1. Field of the Invention

This invention relates to a method of manufacturing a guidewire with an extrusion jacket, and more particularly, to a method of manufacturing a discrete length guidewire of varying thickness. The invention also relates to a method of manufacturing a discrete length guidewire with a helical stripe on the extrusion jacket.

2. Description of the Related Art

Medical guidewires are generally used for navigating through internal passageways of a body. A typical guidewire includes a corewire having a proximal shaft of constant diameter and a taper section of progressively narrowing diameter leading to a distal tip. In order to prevent damage to the body, the guidewire typically includes a relatively soft plastic jacket on the outer surface. The distal end of a guidewire is introduced into a body by a physician through an opening in the body. The physician manipulates the tip of the guidewire through the body to a site to be treated. A catheter or other medical device is usually advanced over the guidewire to the treatment site, and the guidewire is then removed.

Current methods of manufacturing a guidewire with an extrusion jacket have certain drawbacks. Current methods utilize a continuous spool of corewire during the tapering of sections into the corewire, as well as during the extrusion of a plastic jacket onto the corewire. The use of a continuous spool of corewire during tapering and for extruding a jacket onto the corewire is complex and cumbersome. It is difficult to grind a continuous spool of corewire with a varying tapered diameter.

One method of producing a spool of continuous corewires involves the use of acid to etch a taper onto the corewire. The etching method, however, raises environmental concerns. Therefore, for the above reasons, the current methods for manufacturing a continuous tapered corewire are less than desirable.

After the continuous spool of corewire is manufactured and ground, a plastic jacket is typically applied to the outside surface of the corewire. The current methods utilized in applying a plastic jacket to a continuous spool of corewire have certain drawbacks. A typical method of jacketing a continuous corewire also uses a pay-off spool and take-up spool. In this method, the corewire unwinds from a pay-off spool and is then led through a crosshead with a jacket extruder. As the corewire passes through the crosshead, a jacket is extruded onto the corewire. The jacket is then cooled, and the wire is either respooled onto a take-up spool or cut to a predetermined length. After the corewire is cooled, therefore, additional steps, such as cutting the corewire to a length, are required in order to obtain a usable discrete length guidewire. There is a need therefore for a method of extruding a jacket on a corewire which substantially obviates these drawbacks.

Some jackets of conventional guidewires include a helical stripe to make it easier for a surgeon to see that the guidewire is being longitudinally displaced in the opening of the human body. The current method for applying a jacket having a helical stripe to a corewire also has certain drawbacks. In order to obtain a guidewire with a helical stripe, a heat shrinkable hollow tube is used. The heat shrinkable tubing is manufactured by extruding a longitudinal stripe on the hollow tube and then heating, twisting, and cooling the hollow tube. This heat shrinkable tubing can then be heat shrunk onto a corewire to form the jacket of the corewire. This process of heat shrinking the tubing on a corewire, however, does not provide a very strong connection between the jacket and the corewire. Therefore, this can result in a guidewire in which undesired movement occurs between the corewire and the jacket. Moreover, only a limited number of materials are suitable for heat shrinkable tubing, thereby limiting the type of materials that can be used for the jacket. There is a need therefore for a method of manufacturing a guidewire with a jacket having a helical stripe which substantially obviates these problems.

SUMMARY OF THE INVENTION

The advantages and purposes of the invention will be set forth in part in the description which follows, and in part will be obvious from the description, or may be learned by practice of the invention. The advantages and purposes of the invention will be realized and attained by means of the elements and combinations particularly pointed out in the appended claims.

To attain the advantages and in accordance with the purposes of the invention, as embodied and broadly described herein, the invention includes a method of manufacturing a guidewire having a discrete length. The method includes the steps of: feeding a first end of a corewire into an extrusion device; gripping the first end of the corewire with a gripping apparatus; and extruding a first extrusion material onto an outer surface of the corewire while the gripping apparatus pulls the corewire through the extrusion device to form an extrusion jacket on the outer surface of the corewire. The corewire has a predetermined length corresponding to a length of the guidewire In another aspect, the invention includes the above method and the additional step of extruding a visually distinct second extrusion material on the jacket of the corewire while the gripping apparatus pulls the corewire through the extrusion device. During the step of extruding the second extrusion material, the above method further includes the step of rotating the gripping apparatus to rotate the corewire so that the second extrusion material forms a helical stripe on the jacket of the corewire.

In a further aspect of the invention, the invention includes a corewire to be used in manufacturing a guidewire. The corewire includes: a first end section of a substantially constant diameter; a tip section having a diameter less than the first end section diameter; and a second end section of a substantially constant diameter, the second end section diameter being greater than the diameter of the tip section.

In a yet further aspect of the invention, the invention includes an apparatus for manufacturing a discrete length guidewire having an extrusion jacket. The apparatus includes: a first extruder for supplying a first extrusion material onto an outer surface of a corewire to form an extrusion jacket; and a gripping apparatus for gripping a portion of the corewire that has passed through the first extruder, the gripping apparatus being capable of imparting a motion on the corewire as the corewire passes through the first extruder. The gripping apparatus is capable of varied movement to change a physical characteristic of the extrusion jacket.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

In accordance with the present invention, a method for manufacturing guidewires, and particularly discrete length guidewires, is provided. The method for manufacturing discrete length guidewires typically includes feeding a first end of a corewire into an extrusion device; pulling the corewire through the extrusion device, and extruding an extrusion material onto an outer surface of the corewire. In a particular preferred embodiment, a gripping apparatus grips the first end of the corewire and pulls the corewire through the extrusion device to form an extrusion jacket on the outer surface of the corewire.

An apparatus 10 for performing the method of manufacturing, as embodied herein and shown in FIGS. 1-7, includes an extrusion device including an extruder 12, an adapter 14, and a crosshead 16. The extruder 12 can be any known device for providing an extrusion material 30 to an adapter. A typical extruder includes an extrusion screw 13 and barrel 15 as shown in FIGS. 1-6. The screw 13 is located inside the cylindrical barrel 15 so that rotation of the screw 13 causes the extrusion material 30 to flow to the adapter 14.

Figure 7:
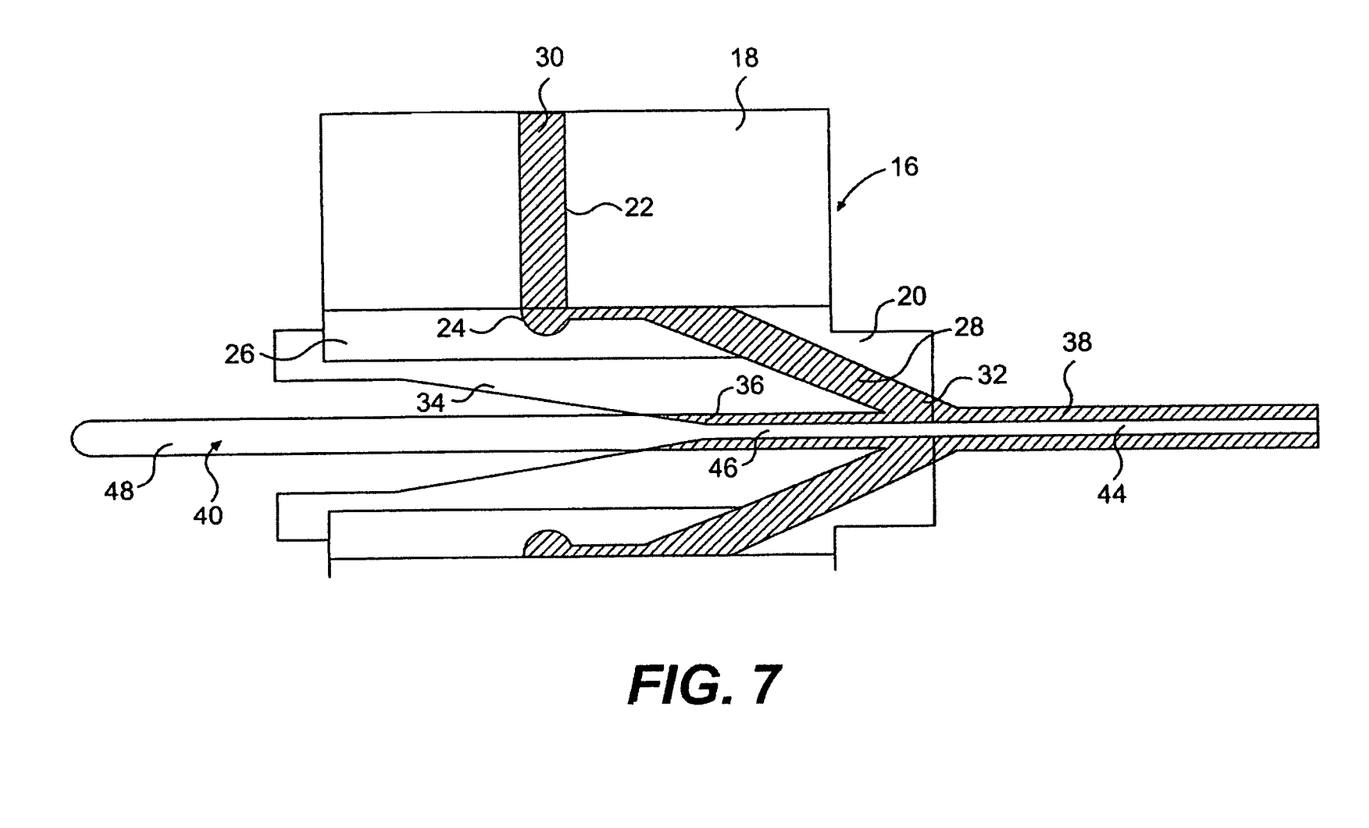
FIG. 7 is a cross-sectional side view of the crosshead of the apparatus of FIG. 1 and a corewire therein according to an embodiment of the invention.

The adapter 14 is in the shape of a funnel to provide the extrusion material 30 to the crosshead 16 from the extruder 12. Crosshead 16 includes a cylindrical outer portion 18 and an inner portion or die 20. As best shown in FIG. 7, the cylindrical outer portion 18 includes a supply port 22 for receiving extrusion material 30. The extrusion material 30 travels from the supply port 22 to a circumferential groove 24 in a flow diverter portion 26 of the crosshead. The circumferential groove 24 extends around the outer circumference of the flow diverter 26 as shown in FIG. 7. The extrusion material 30 then flows through a conical space 28 between the flow diverter 26, tip 34, and die 20 of the crosshead, as best shown in FIG. 7. The extrusion material is then applied to the outside diameter of a discrete length corewire 40 at extrusion material supply opening 32, as will be described in greater detail below.

The die 20 of the extruder 16 further includes a tapered opening 34 for entrance of the corewire. The tapered opening 34 has a conical inner surface that leads to a cylindrical inner surface defining a hole 36. The cylindrical inner surface defining hole 36 guides the corewire through the crosshead.

Figure 1:
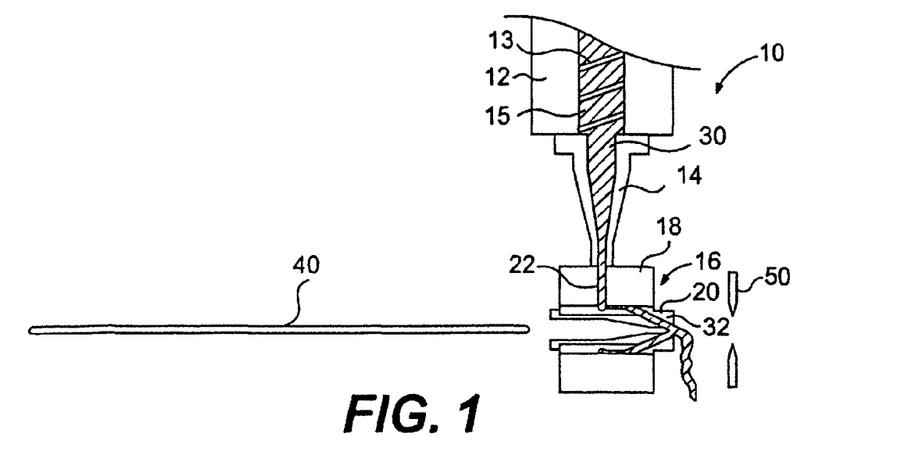
FIG. 1 is a partial cross-sectional side view of an apparatus for manufacturing a discrete length guidewire according to an embodiment of the invention, prior to insertion of a corewire into a crosshead.

According to an embodiment of the present invention, the method for manufacturing a discrete length guidewire will be described with reference to FIGS. 1-6. FIG. 1 shows the extrusion apparatus 10 and corewire 40 prior to insertion of the corewire into the crosshead 16. Corewire 40 is shown as being a constant diameter corewire. A preferable corewire, however, is the corewire shown in FIG. 7-9. Details of the preferred shape of that corewire will be discussed below. Any shape corewire, however, may be used in the extrusion methods and apparatus of the present invention. The discrete length corewire is typically ground into the desired shape by the use of a centerless grinding technique known in the art or any other suitable method.

Prior to and during extrusion, a predetermined amount of extrusion material 30 is allowed to flow through the extrusion device. Control of the amount of material 30 may be performed by any suitable control apparatus or method known in the art. Preferably, the extrusion device is controlled by computer controls with an interface control panel. The desired flow speed of the extrusion material is a function of a variety of factors such as the rotational speed of the extrusion screw 13, the temperature of the extrusion material, the properties of the particular extrusion material, and the tooling design.

Once the extrusion material begins to flow, the first end of corewire 40 is fed into the extrusion device at the tapered opening 34 of the crosshead 16 and then into the hole 36 of the crosshead 16. The guidewire may be manually fed into the crosshead by an operator or automatically fed into the extrusion device by an automatic payoff system. Once the first end of the corewire 40 reaches the extrusion material supply opening 32, the extrusion material 30 adheres to the outside surface of the corewire 40. The extrusion material 30 forms an extrusion jacket 38 on the outer surface of the corewire, as best shown in FIG. 7. The jacket 38 is preferably concentric with the central axis of the corewire. The extrusion material can be any of the known materials suitable for extrusion and insertion into the human body, such as, but not limited to, polyurethane, polyethylene, nylon, pebax, and polycarbonate. The extrusion material may also include additives that are appropriate for the specific intended use of the guidewire. For example, fillers such as tungsten, barium sulfate, bismuth trioxide, and bismuth subcarbonate are often added for radiopacity. Other fillers may be used in order to increase characteristics such as surface friction, density, and lubricity.

It is desirable for the extrusion material to closely adhere to the outside surface of the corewire so that the extrusion jacket 38 cannot easily come off of the corewire. There are several methods for increasing the adhesion between the extrusion jacket and the corewire. In a first method, a polymer is added to the extrusion jacket material in order to increase the adhesion between the extrusion jacket and corewire. In a second method, the corewire is coated with silane prior to insertion into the crosshead. The silane promotes adhesion between oxides formed on the corewire and the extrusion material. Other methods of increasing the adhesion between the extrusion jacket and corewire may also be used.

Figure 2:
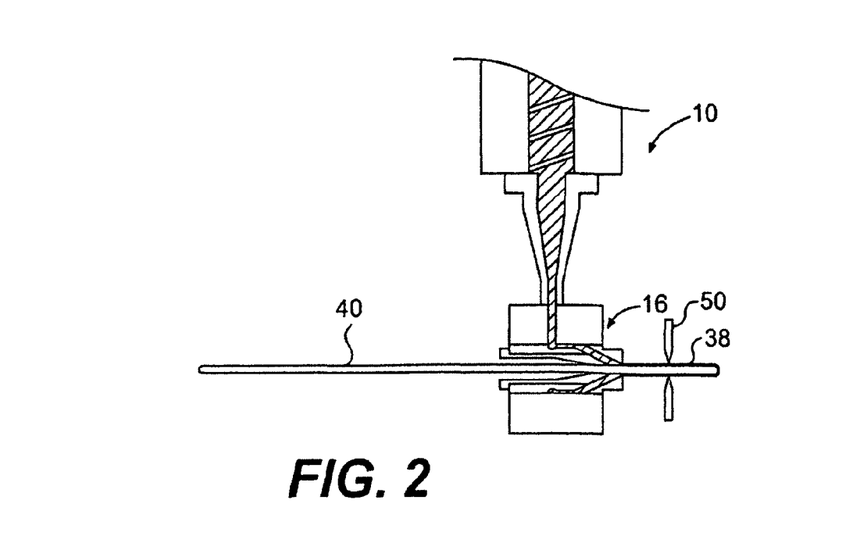
FIG. 2 is a partial cross-sectional side view of the apparatus of FIG. 1, with a gripping apparatus gripping onto an extruded corewire.

After the first end of the corewire 40 passes through the crosshead and the jacket 38 begins to extrude onto its outer surface, a gripping apparatus 50 clamps onto the jacket 38 at the first end of the corewire, as shown in FIG. 2. The gripping apparatus 50 may be a pneumatic gripper, however any other suitable gripping apparatus is also acceptable. The gripper is mounted on a carriage (not shown) which traverses along a linear rail (not shown). The motion of the carriage may be controlled by a stepper or servo motor, or any other suitable means to control the carriage motion.

The guidewire can be pulled through the crosshead 16 by the gripping apparatus 50 at a variety of speeds. The effect of a variation in guidewire speed will be discussed further. The controller also controls the travel distance of the gripping apparatus 50. As the gripping apparatus 50 is translated to the right in FIG. 3, the extrusion jacket 38 is extruded onto the outer surface of the corewire.

Figure 3:
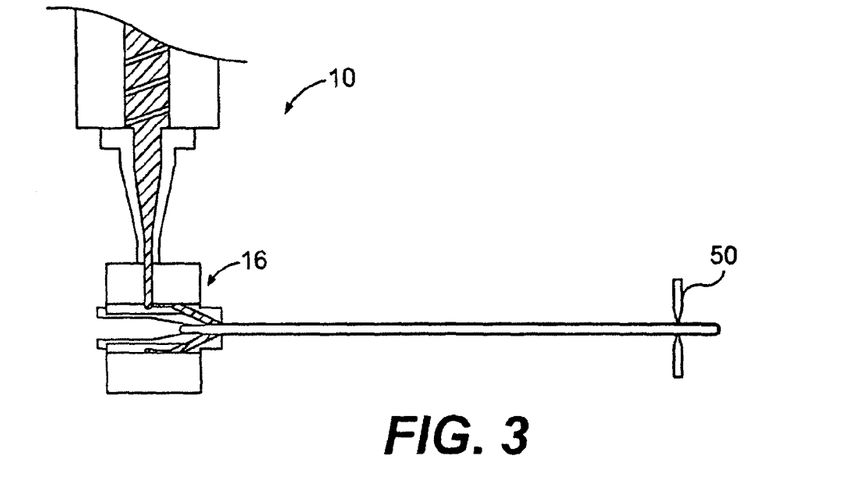
FIG. 3 is a partial cross-sectional side view of the apparatus of FIG. 1, prior to removal of the corewire from the crosshead.
Figure 4:
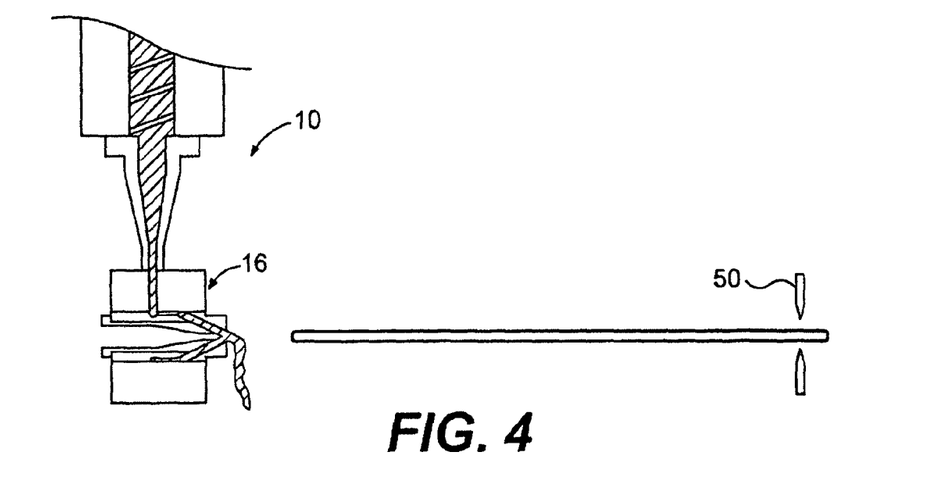
FIG. 4 is a partial cross-sectional side view of the apparatus of FIG. 1, after removal of the corewire from the crosshead.

As the corewire 40 with extruded jacket 38 is translated to the right in FIG. 3, the entire corewire 40 is pulled through the crosshead 16. The jacket and corewire then may be placed in and pulled through a cooling trough by the gripping apparatus. Cooling troughs are well known in the art, therefore details of the cooling trough are not shown. After the entire corewire with the extruded jacket has passed through the cooling trough, the guidewire is released by the gripping apparatus, as shown in FIG. 4, and placed into a holding tray (not shown). The cycle is then repeated for subsequent corewires to manufacture additional guidewires. Alternate methods of translating corewires through the crosshead will be described later.

Figure 5:
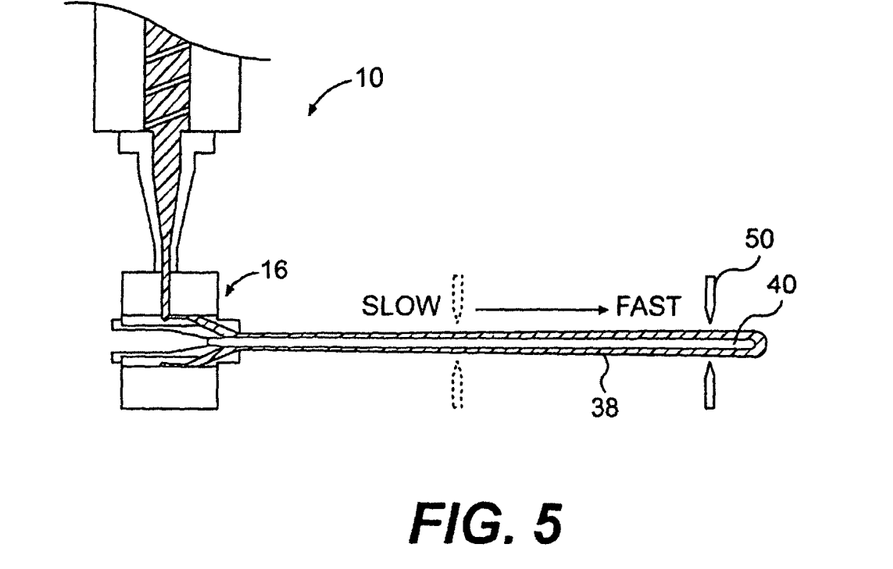
FIGS. 5-6 are partial cross-sectional side views of the apparatus of FIG. 1, showing an extruded corewire that resulted from varying the linear speed of the gripping apparatus according to an embodiment of the invention.
Figure 6:
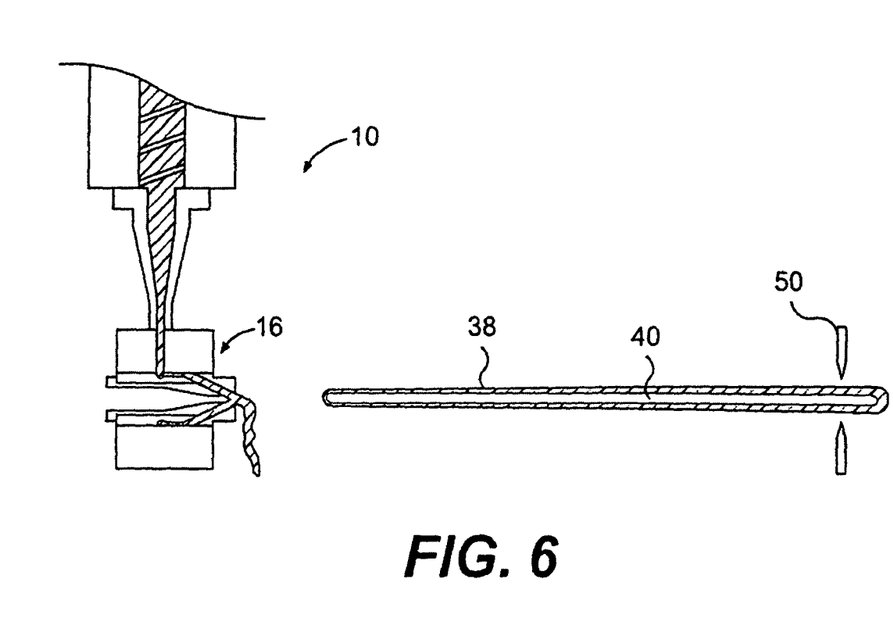

A variation in the speed of the corewire passing through the crosshead will vary the thickness of the jacket along the guidewire length. FIG. 5 shows an example of the results of varying the linear speed of the corewire through the crosshead. In FIG. 5, the corewire was initially pulled through the crosshead at a constant speed. Therefore, the thickness of the jacket is constant in the initial section of the corewire, i.e., the section to the right in FIG. 5. Thereafter, the speed of the gripping apparatus motion was increased to increase the speed of the corewire through the crosshead. The increase in linear corewire speed resulted in a smaller thickness extrusion jacket. Therefore, the diameter at the second end portion of the guidewire, i.e., the portion to the left in FIG. 5, is smaller than the diameter at the first end of the guidewire. The result of such a variation in corewire speed is shown in FIG. 6. In this case, the gripping apparatus (and therefore the corewire) was displaced at a substantially constant acceleration, resulting in the outside diameter of the guidewire jacket having a smooth taper. The speed of the gripping apparatus and therefore the speed of the corewire through the crosshead may be changed at any rate to result in a guidewire having a desired shape. For example, a constant diameter corewire may be used to form a guidewire with a tapered section leading to a distal tip, as shown in FIGS. 5 and 6.

Figure 8:
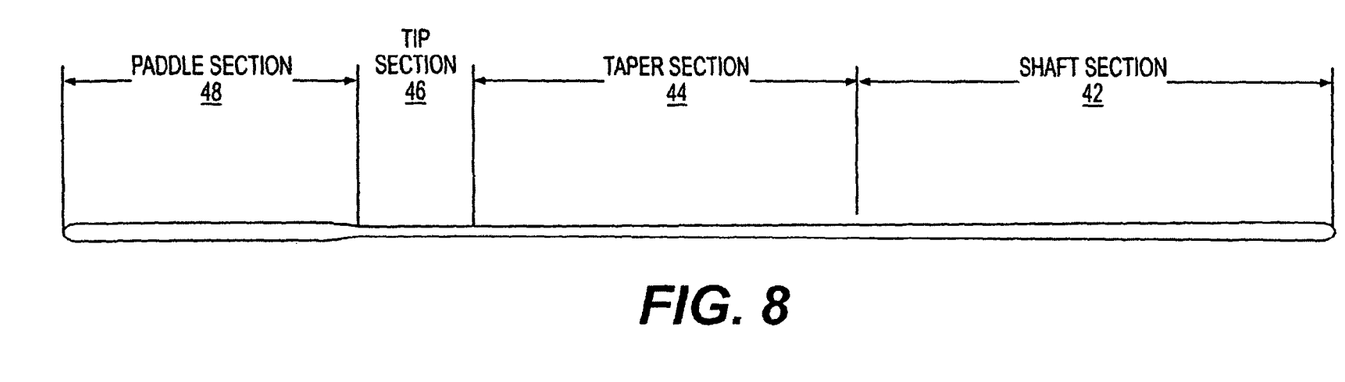
FIGS. 8-9 are corewires according to an embodiment of the invention.
Figure 9:
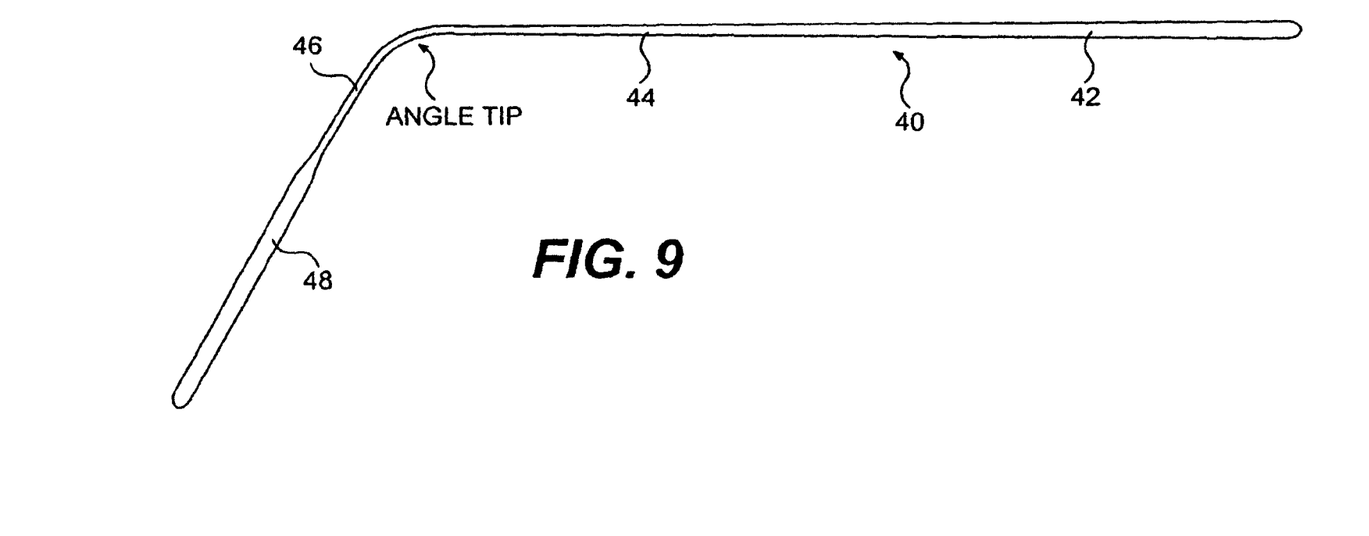

The corewire of a guidewire can consist of a variety of shapes, and a corewire of any such shape can be used in the extrusion process of the present invention. For example, a corewire for use in the methods according to the present invention is shown in FIGS. 7-9. The corewire 40 has a number of regions with different diameter profiles. The corewire 40 includes a main shaft section or first end section 42 of substantially constant diameter. The end referred to as the first end section 42 is the portion of the corewire which is initially inserted into the crosshead. As shown in FIGS. 8-9, first end section 42 of constant diameter extends to a tapered section 44. The beginning of tapered section 44 has an outer diameter equal to the outside diameter of the first end section 42. The diameter of the taper portion 44 decreases until it reaches the diameter of a tip section 46. The tip section 46 has a substantially constant diameter, preferably of a smaller diameter than the first end section 42. The tip section 46 preferably tapers to a second end section or paddle section 48 of a substantially constant diameter. The diameter of second end section 48 is preferably greater than the diameter of the tip section 46, for reasons which will be discussed below.

The paddle section 48 enables the crosshead to apply a concentric jacket of extrusion material on the tip section 46 of the corewire. As shown in FIG. 7, the diameter of the tip section 46 of the guidewire is substantially smaller than the diameter of hole 36 defined by the inner cylindrical surface of the crosshead. Therefore, there is a gap between the outside surface of the corewire 40 and the inner cylindrical surface of hole 36. This gap is filled with extrusion material as shown in FIG. 7. It is desirable that the extrusion material be applied evenly around the corewire, including the tip section 46. Therefore, it is desirable to have a centering system which centers the tip section 46 in the crosshead in order to provide a uniform jacket 38 around the tip section 46. The paddle section 48 serves as the centering system once the paddle section enters hole 36 as shown in FIG. 7. The diameter of paddle section 48 is only slightly smaller than the inner diameter of hole 36. Therefore, because the tip section 46 is concentric with the paddle section 48, the tip section 46 will be centered in the inner cylindrical surface 36 of the crosshead and the jacket applied to the tip section 46 will also be concentric.

The paddle section 48 will serve the function of centering the tip section even if the corewire has been bent. It is often desirable to use an angled tip corewire in order to better manipulate through the human body. For certain operations, it is best to have a predetermined bend on the corewire tip prior to insertion into the human body. However, because of the properties of the corewire material, it is often necessary to heat the corewire to high temperatures in order to bend the corewire to the desired angle. For example, linear elastic materials such as nickel titanium alloy have linear-elastic characteristics which require heating in order to bend the tip of the corewire into an angled or J shape. Other suitable materials include, but are not limited to, super-elastic materials, stainless steel, titanium, and composite corewires of fiberglass or carbon-fiber. Therefore, the corewire that is to be inserted into the crosshead may have a predetermined bend in it, as shown for example in FIG. 9 where tip section 46 has a bend. The paddle section 48 allows the crosshead to apply a concentric extrusion jacket on the corewire, even though the corewire has a significant bend in it.

Even with a significant bend in the corewire 40, the corewire 40 will begin to straighten as it is translated through the crosshead 16. As the tip section 46 first enters hole 36 of the crosshead 16, the bend in the tip section 46 will cause the tip section 46 to be off-center from the center of hole 36. However, as the corewire 40 is pulled through the crosshead 16, the paddle section 48 will abut the tapered opening 34 of the crosshead and begin to straighten the corewire 40. As the corewire 40 is further drawn through the crosshead 16, the beginning of the paddle section 48 will enter hole 36 of the crosshead 16, straightening the corewire 40 and centering the tip section 46, as shown in FIG. 7. The tip section 46 will now receive a concentric extrusion jacket 38 as it passes through the crosshead 46. After the tip section 46 and the paddle section 48 have completely exited the crosshead 16, the corewire 40 may regain some or all of its previous bend, depending, for example, on the properties of the corewire and extrusion materials and the amount of bend. Alternately, also depending on the materials and the amount of bend, the corewire may remain straight.

The provision of a paddle section on the corewire is particularly useful when extruding an extrusion jacket on a corewire having an angled tip. The paddle section assists in centering the corewire in the crosshead hole so that the extrusion jacket will be concentric with the corewire. The provision of the paddle section may also be helpful in improving centering in a substantially straight corewire that has minor bends. It may be possible, however, to have a completely straight corewire that requires no paddle section for centering. In such a corewire without a paddle section, the distalmost end of the corewire will be the tip section.

Figure 10:
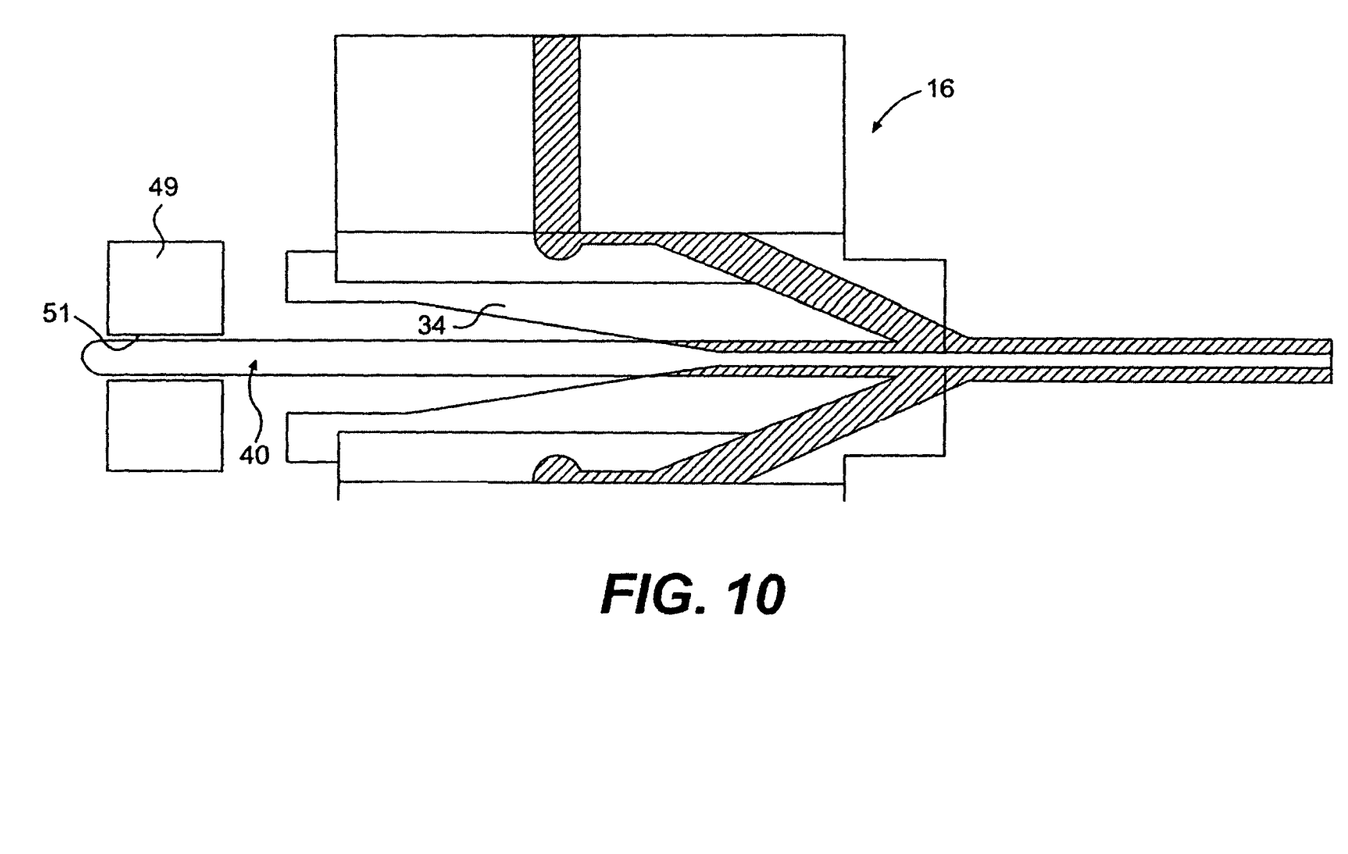
FIG. 10 is a cross-sectional side view of the crosshead of FIG. 7 with a guiding tube according to an embodiment of the invention.

In an alternate embodiment of the present invention, the crosshead may include a guiding member for centering the core wire in the crosshead. As embodied herein and shown in FIG. 10, a guiding member in the shape of a guiding tube 49 is located adjacent the opening of crosshead 16 and receives corewire 40. The remainder of the crosshead and the corewire are identical to the crosshead and corewire illustrated in the embodiment shown in FIGS. 7-9. The guiding tube 49 has a cylindrical opening 51 that is coaxial with hole 36 of the crosshead 16. The coaxial relationship between the guiding tube 49 and the hole 36 will ensure that the shaft section 42 of the corewire 40 will initially be inserted in the crosshead in a coaxial manner, in addition to the ensuring that the corewire will remain centered in the crosshead throughout the extrusion process. The first end section 42 of the corewire 40 initially is inserted through the guiding tube, then hole 36 of the crosshead. As the corewire 40 is pulled through the crosshead, the bent portion of the tip section 46 will enter into the cylindrical opening 51 of the guiding tube 49. The bent portion of the tip section 46 will abut against the inner surface of the cylindrical opening 51 of the guiding tube 49 and straighten the corewire 40. In this manner, the straightened corewire will be fed through the crosshead 16. The guiding member is not limited to being a tube 49, but may be any other suitable size and shape that centers the corewire in the crosshead.

To complete the manufacture of the guidewire, after the corewire with jacket is pulled through the cooling trough and placed in a holding tray, as previously described, the paddle section 48 is removed, leaving tip section 46 as the distalmost portion of the final guidewire. After the paddle section is removed, it is desirable that the distalmost portion of the tip section of the final guidewire be provided with a closed tip formed of polymeric or resin-like material similar or identical to the extrusion material. The provision of such a tip reduces the likelihood of damage to the body which would occur if the metal corewire was exposed. There a variety of methods of providing an extrusion-like material to the distalmost portion of the final guidewire after the paddle section has been removed. In a first method, the guidewire is heated and a tip is molded onto the distalmost portion of the guidewire. The molded tip can be made out of the same material as the extrusion jacket, or out of a different material. In a second method, a tip is heat formed onto the distalmost portion of the guidewire from the existing extrusion material of the jacket. When the guidewire is heated, the extrusion material of the extrusion jacket will flow towards the distal end of the guidewire to form a tip. A third possible method is to dip the distalmost end of the guidewire into a glue or resin solution. The glue or resin will then bond to the extrusion material and tip of the corewire to form a smooth tip. In the third method, the material in which the guidewire is dipped could also be made out of the extrusion material. In a fourth method of providing an extrusion-like material to the distalmost end of the tip section, the extrusion material is recessed back from the distalmost end of the corewire before or as the paddle section is cut off. Therefore, after the paddle section is cut off, the resulting guidewire has the distalmost end slightly recessed in the extrusion material jacket. The extrusion material jacket projects beyond the end of the corewire. The tip of the guidewire can then be heated so that the projecting extrusion jacket melts around the distalmost end of the corewire to form a tip of the extrusion material.

It may also be desirable to remove a portion of the proximalmost tip of the guidewire. In such a case, it is desirable to provide a closed tip formed of polymeric or resin-like material using any of the methods described above for the distalmost portion.

The above method is described as using a single gripper to pull the guidewire through the crosshead. However, alternate methods of translating consecutive guidewires through the crosshead are also acceptable. In a first alternate method, a second gripper is provided in addition to the first gripper. The first gripper will grip the first guidewire as previously described. Once the first guidewire is pulled completely through the crosshead, a second guidewire will typically project from the crosshead. At this point, since the first gripper is still gripping the first guidewire, a pause in the linear translation or an additional axial spacing between the guidewires will be required before the first gripper can translate back to the crosshead and grip the second guidewire. It is undesirable to have a long delay between each guidewire being translated through the crosshead. The axial spacing is also undesirable because a large amount of extrusion material is wasted in the regions between the guidewires. The provision of a second gripper helps to alleviate these problems. The second gripper can grasp the second guidewire immediately upon the second guidewire projecting through the crosshead. Therefore, consecutive guidewires can have minimal spacing therebetween, and there is no need for a pause between insertion of guidewires.

Figure 11:
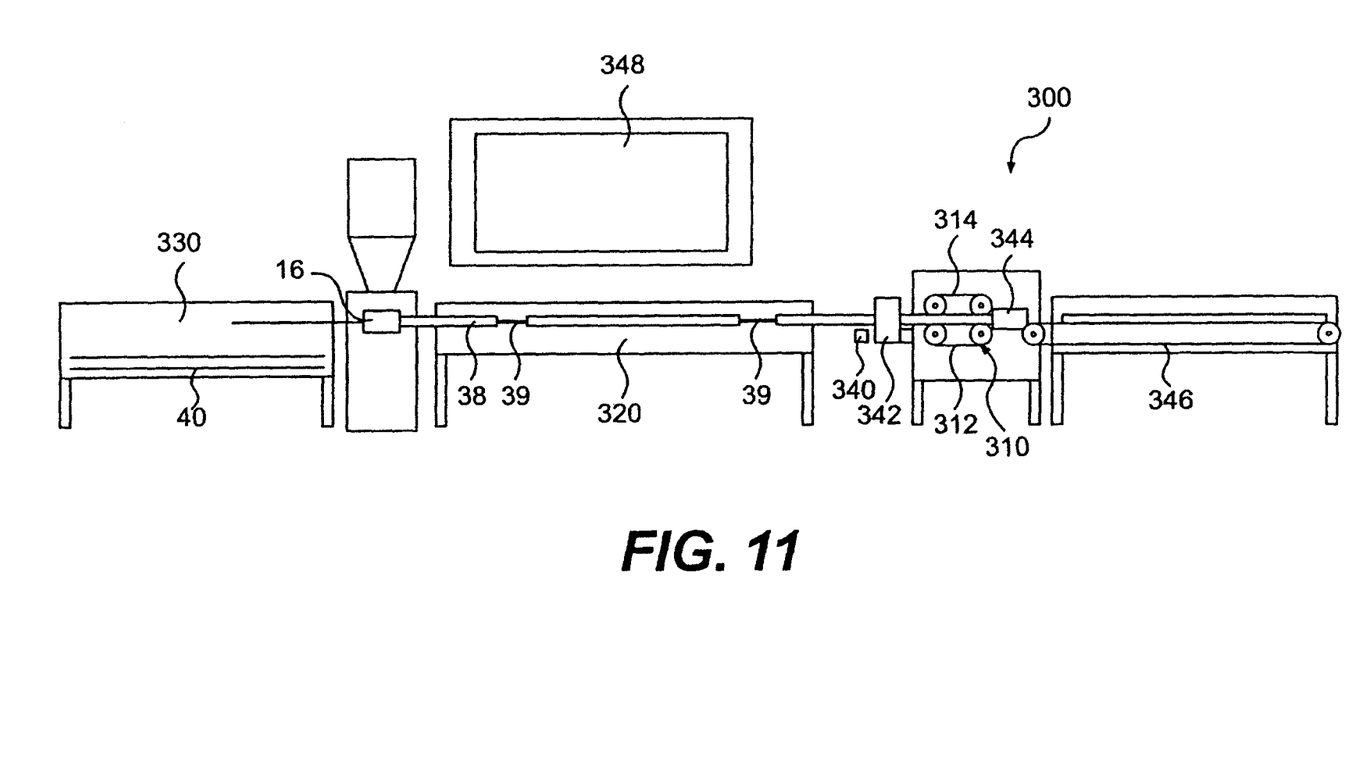
FIG. 11 is a schematic side view of an apparatus for manufacturing a discrete length guidewire according to an embodiment of the invention with a conveyor system.

In a method according to another embodiment of the present invention, a conveyor system translates the guidewires through the crosshead, as opposed to the grippers described in the above embodiment. FIG. 11 illustrates one example of a conveyor system that can be used with the present invention. The conveyor system 300 preferably is located downstream, i.e., after the crosshead 16. The conveyor system preferably includes a puller comprising at least one belt-like conveyor, and may be designed to engage the bottom of the guidewire, or both the bottom and the top of the guidewire. As shown in FIG. 11, the puller 310 includes two belt-like conveyors 312 and 314 for engaging the top and bottom of the guidewire. In addition, a conventional water bath 320 is provided between the crosshead and conveyor system. The water bath cools the extrusion jacket after the corewire has left the crosshead. The water bath is typically at least several feet long, the water bath length being a factor of the speed at which the guidewires are fed through the crosshead, the temperature of the newly extruded extrusion material, and the temperature of the cooling water in the water bath.

The initial step of the method employing the conveyor system and water bath is to form a long strand of entirely extrusion material that will be used to pull the initial guidewires through the crosshead and water bath to the conveyor system. To form this long strand, extrusion material is extruded into the hole in the crosshead without insertion of a corewire. The initial extruded strand is then pulled through the water bath and inserted between the conveyors 312 and 314 of the puller 310. The initial extruded strand is pulled through the water bath and into the puller by any suitable means, such as the manual use of a pair of pliers to grip the strand. Once the initial extruded strand is sufficiently inserted into the puller, the puller pulls the long initial strand of extrusion material through the crosshead and water bath.

The first corewire then is inserted into the crosshead via a payoff system or manual insertion, while extrusion material continues to flow into the crosshead. FIG. 11 illustrates one example of payoff system 330 for inserting the corewire into the crosshead. The corewire thereby has an extrusion jacket 38 extruded on it as it passes through the crosshead 16. The extrusion jacket is integrally connected to the long strand of extrusion material so that the strand (through action of the conveyor) pulls the corewire through the crosshead, then through the water bath, until the corewire reaches the puller of the conveyor system. A second corewire is inserted into the crosshead, leaving a small amount of axial space between the first and second corewires. Because extrusion material continues to flow between consecutive corewires, a strand of extrusion material 39 extends between consecutive guidewires, helping to pull the upstream guidewire through the crosshead. This results in a series of connected guidewires with a small amount of extrusion material 39 located therebetween. The extrusion material located between the guidewires is later removed, along with the paddle section of the guidewires. The scope of the present invention includes other alternate methods besides those described above to translate a corewire through the crosshead.

As illustrated in FIG. 11, the system may further include a detector 340 for sensing the location of the guidewires. Detector 340 may be any suitable detection device, such as a metal detector. The metal detector, in one embodiment, is located immediately downstream from the water bath 320. A laser micrometer 342 may be located after the metal detector for sensing the dimensions and position of the guidewire. In one embodiment, the laser micrometer is located immediately before the puller 310. The detector and/or micrometer aid in the precise cutting of the guidewires, and particularly the extrusion material 39 between adjacent guidewires. A cutting device 344 may be included immediately after the puller 310 for cutting the extrusion material 39 between adjacent guidewires.

Based on the speed of the puller and the position information from the metal detector and/or laser micrometer, a feedback control system activates the cutter at a predetermined time. This feedback control system also utilizes information from the metal detector and laser micrometer to control the outer diameter of the extrusion jacket of the guidewire by adjusting various factors such as the linear speed of the puller or conveyor and/or the rotational speed of the extrusion screw 13. The conveyor system shown in FIG. 11 also includes an additional conveyor 346 located downstream from the pulley 310. After the extrusion material between the guidewires is cut by cutting device 344, the guidewire is fed onto the additional conveyor 346 by the puller 310. The conveyor 346 takes the guidewire with the extruded jacket from the puller 310, and translates the guidewire to the next station. As illustrated in FIG. 11, a control panel display 348 may be included in order to display control information.

The above methods will produce a discrete length guidewire with a minimum number of steps and processes. Additionally, the discrete length guidewire can be manufactured with a predetermined bend. The above methods can also be used to manufacture a variety of medical devices other than guidewires. For example, the above methods can be used to extrude material onto the coil of a biopsy device, catheter, stent, snare, or other endoscopic device. The above methods are acceptable for extruding material onto any suitable longitudinal medical device, and is not limited to the examples described above.

Another embodiment of the invention will now be described wherein like or similar parts are identified throughout the drawings by the same reference numerals. This embodiment is directed toward a method for manufacturing a discrete length guidewire with a jacket having a helical stripe. In accordance with this embodiment of the present invention, a method of manufacturing a discrete length guidewire includes extruding a jacket similar to that described above, but further includes the extrusion of a second extrusion material to form a helical stripe on the corewire. Embodiments of the method and apparatus for practicing the method now will be described.

As embodied herein and shown in FIGS. 12-15, the apparatus 110 manufactures a discrete length guidewire with a jacket having a helical stripe. Apparatus 110 includes a first extruder 112 and a first adapter 114. The first extruder 112 and first adapter 114 are substantially identical to the extruder 12 and adapter 14 described above. The crosshead 116 is different than the crosshead 16 described above because crosshead 116 extrudes both a first extrusion material 130 to form the jacket and a second extrusion material 230 to form the jacket stripe. Although the structure of crosshead 116 for extruding the first extrusion material is substantially the same as the structure of crosshead 16, crosshead 116 further includes structure for extruding a second extrusion material to form a stripe. The crosshead 116 allows for a second extruder 212 and a second adapter 214 that contain a second extrusion material 230.

In a preferred embodiment, the second extrusion material 230 is visually distinct from the first extrusion material 130. The second extrusion material is different in color, shade, or otherwise different in appearance, than the first extrusion material. The second extrusion material, however, can be made of the same materials as the first extrusion material, or different materials. The first and second extrusion materials are preferably formed of any of the extrusion materials described above. The first and second extrusion materials may also be provided with the fillers described above. For example, it is often desirable to make the second extrusion material out of material having a different radiopacity than the first material.

Figure 12:
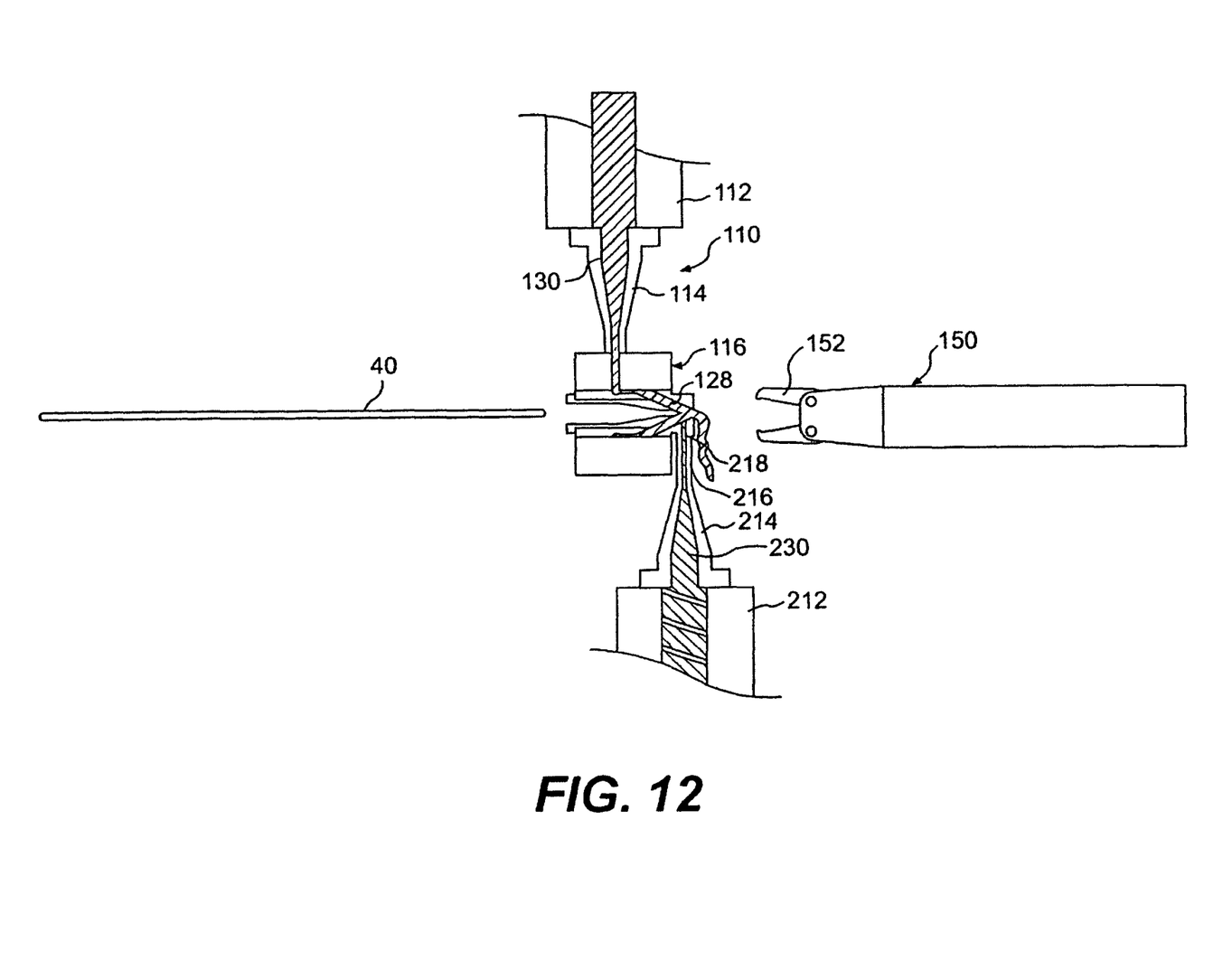
FIG. 12 is a partial cross-sectional side view of an apparatus for manufacturing a discrete length guidewire with a helical stripe according to an embodiment of the invention, prior to insertion of a corewire into a crosshead.

The second extrusion material 230 flows from the second extruder 212 to the second adapter 214. The end of the second adapter 214 has a thin exit port 216 that leads to a second extrusion material port 218 in the crosshead, as shown in FIG. 12. The second extrusion material port 218 is located on the inner surface of the crosshead at the conical groove 128. The second extrusion material 230 is applied to the exterior of the first extrusion material 130. The applied amount of second extrusion material is preferably substantially less than the applied amount of first extrusion material because often only a thin stripe is desired on the outside of the first extrusion material. The amount of second extrusion material applied over the first extrusion material may vary, however, according to the desired thickness of the helical stripe. As with the first extrusion material, control of the applied amount of second extrusion material may be performed by any suitable control apparatus or method known in the art.

The method for creating the jacket and stripe on the jacket will be described in connection with FIGS. 12-15. FIG. 12 shows the apparatus 110 prior to insertion of the first end section of the corewire 40 into the crosshead 116. The corewire 40 can be any type of corewire, including the tapered corewire described above and shown in FIGS. 8-9. The first end section of the corewire 40 is fed into the crosshead 116. As the corewire 40 passes by the conical groove 128, the first extrusion material 130 begins to form a jacket on the outside surface of the corewire 40. As the first extrusion material 130 is extruded onto the outside surface of the corewire, the second extrusion material 230 is dispensed onto the outside surface of the first extrusion material 130.

In order to provide rotation (to obtain a helical shape) and translation to the corewire 40, a rotating gripper 150 with clamps 152 is provided. The rotating gripper 150 clamps on the outside surface of the jacket after the first end of the corewire exits the crosshead. The rotating gripper 150 proceeds to rotate and linearly translate upon gripping the corewire with jacket.

Figure 13:
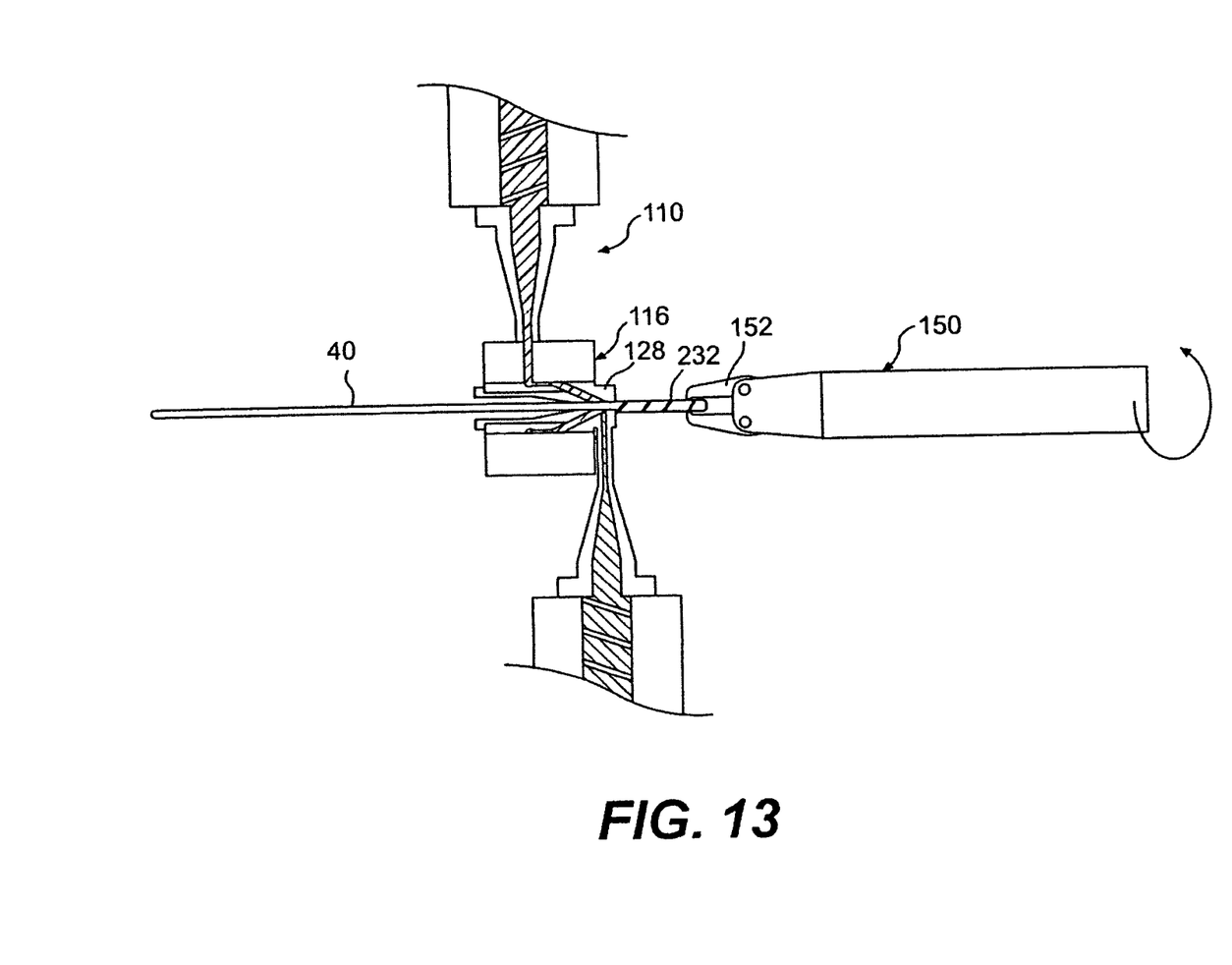
FIG. 13 is a partial cross-sectional side view of the apparatus of FIG. 12, with a rotating gripping apparatus gripping onto an extruded corewire.
Figure 14:
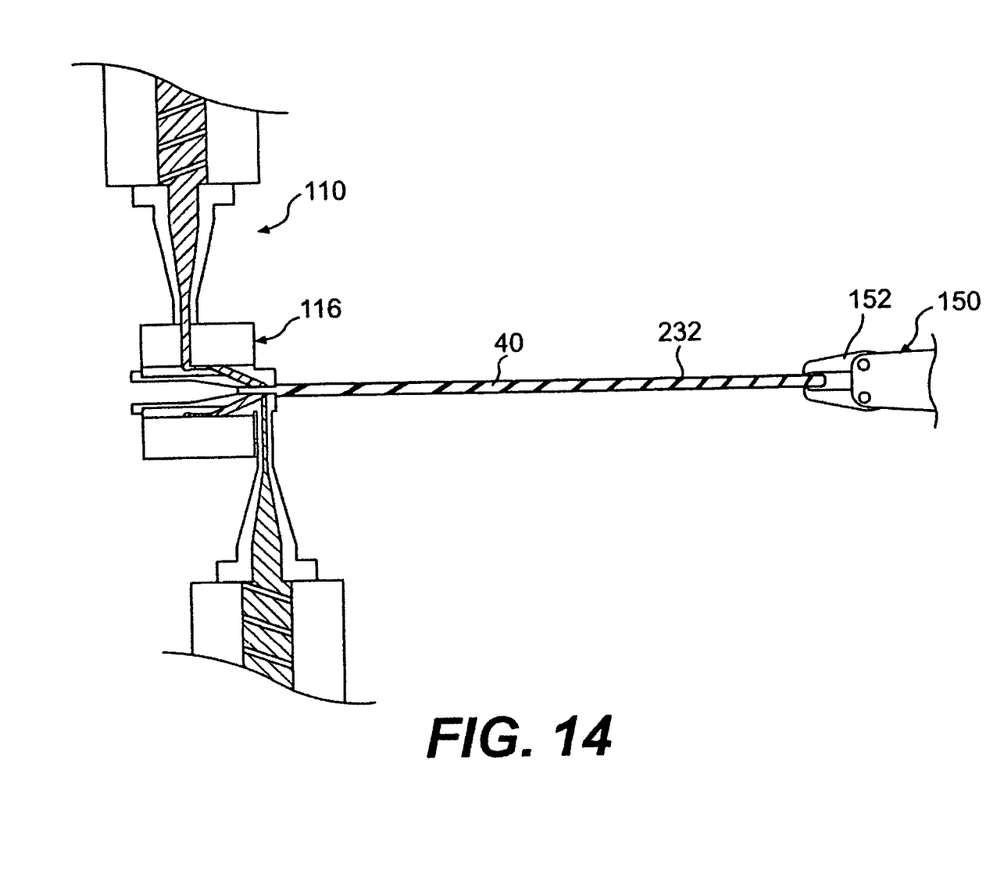
FIG. 14 is a partial cross-sectional side view of the apparatus of FIG. 12, prior to removal of the corewire from the crosshead.
Figure 15:
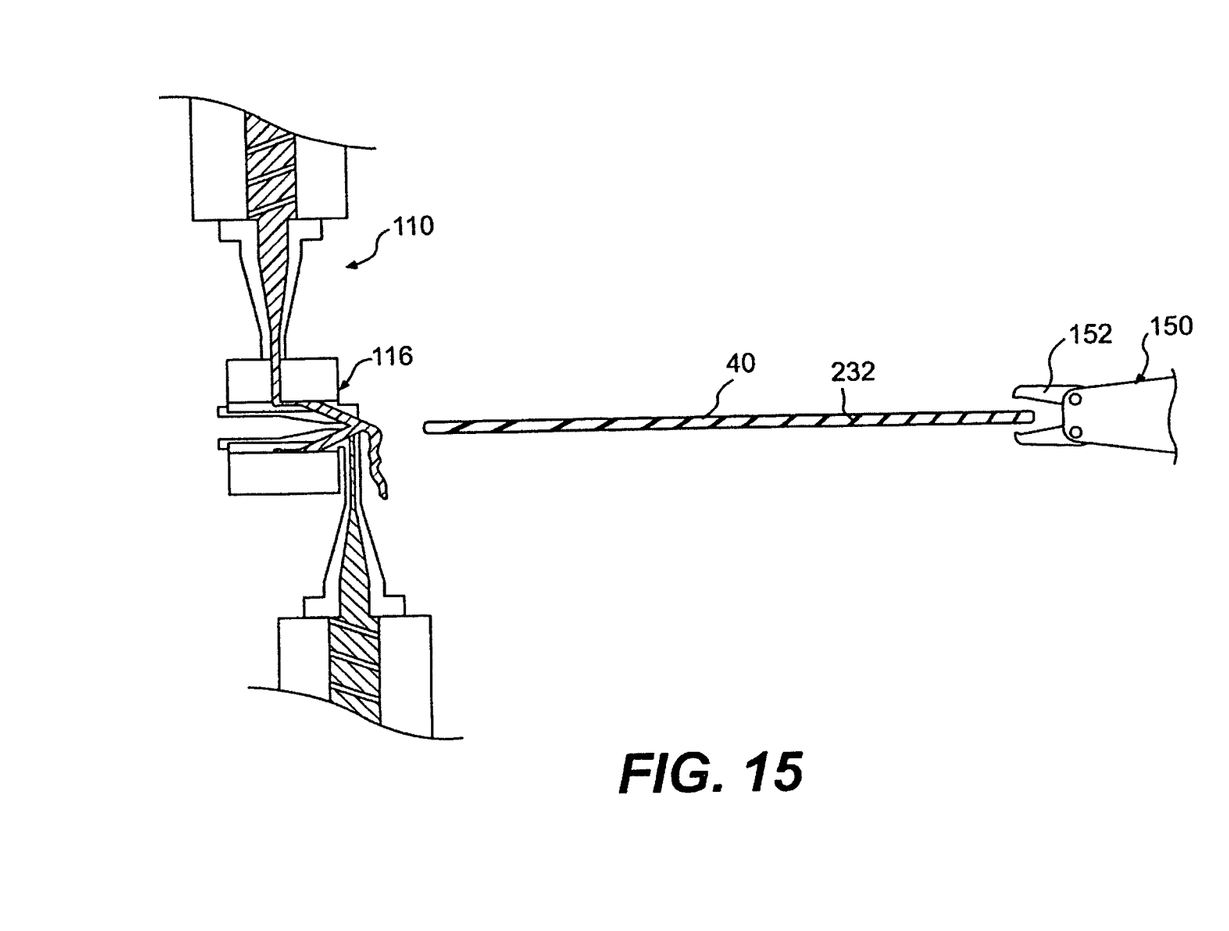
FIG. 15 is a partial cross-sectional side view of the apparatus of FIG. 12, after removal of the corewire from the crosshead.

The rotating gripper 150 is attached to a carriage (not shown) that traverses along a linear rail (not shown) and rotates about the axis of the corewire. Alternately, any other suitable method of rotating and linearly translating the guidewire is also acceptable. The motion of the carriage and gripper may be controlled by a stepper or servo motor, or any other suitable means. The rotational and linear motion of the gripper causes the second extrusion material to form a helical stripe 232 on the outside of the guidewire, as shown in FIGS. 13-15. With a constant rotational and linear speed, the helical stripe 232 will have a constant pitch.

The method also preferably includes varying the linear and/or rotational speed of the rotating gripper to create a stripe with a varying helical pitch. For example, if the rotational speed of the gripper is decreased, the pitch of the stripe (distance between the threads of a helical stripe) will increase. FIGS. 14 and 15 show a guidewire created with decreasing rotation speed to create an increasing pitch on the stripe 232. As shown in FIGS. 14 and 15, the pitch of the stripe 232 increases from the first end section to the second end of the guidewire. The linear speed of the gripper can also be varied. A variation in the linear speed of the gripper and corewire passing through the crosshead will have the same effect as discussed in connection with FIGS. 5 and 6. An increase in the linear speed of the corewire will cause the thickness of the jacket to decrease. In addition, an increase in the linear speed of the corewire will also cause the pitch of the stripe 232 to increase, resulting in greater spacing between adjacent stripes.

The provision of a helical stripe with a variable pitch is useful in the process of inserting or removing a guidewire into and out of the human body. The stripe allows for visual confirmation that the guidewire is being longitudinally displaced. By varying the helical pitch of the stripe along the length of the guidewire, an operator can visually determine the depth of the guidewire. Because the proximal end might have a low pitch, while the distal end has a high pitch, it is possible to estimate how far the guidewire has been inserted.

The remainder of the manufacturing method corresponding to the embodiment of FIGS. 12-15 is substantially identical to the method described above. The corewire with the jacket is pulled through a cooling trough (not shown). The completed guidewire is released by the gripper and placed in a holding tray (not shown). The cycle is then repeated for the next corewire. A number of discrete length guidewires having a variable pitch helical stripe can thus be manufactured.

In an alternate method of manufacturing a discrete length guidewire with a jacket having a helical stripe, the crosshead 116 rotates instead of the gripper 150. In such a configuration, the relative rotation of the crosshead relative to the corewire causes a helical stripe to be formed in the extrusion jacket.

It will be apparent to those skilled in the art that various modifications and variations can be made in the apparatus and method of manufacturing a discrete length guidewire, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A discrete length corewire to be used in manufacturing a guidewire, comprising:
    a first end section of a substantially constant first end section diameter;
    a tip section having a diameter less than the first end section diameter;
    a tapered section between the first end section and the tip section;
    a second end section of a substantially constant second end section diameter detachably connected to a distal end of the tip section, the second end section diameter being greater than the diameter of the tip section and the first end section diameter;
    wherein the second end section is configured to center the tip section as the corewire is passed through an extrusion apparatus and the second end section is configured to be detached from the corewire so as to define the tip section as a distal tip of the corewire; and
    a concentric jacket of extrusion material extruded onto an outer surface of the tip section;
    wherein an outer diameter of the jacket is the same as or greater than the second end section diameter.

2. A corewire of claim 1, wherein the diameter of the tip section is substantially constant.

3. A corewire of claim 1, wherein the tip section has a predetermined bend.

4. A method of manufacturing a discrete length guidewire, comprising:
    providing a discrete length corewire comprising:
        a first end section of a substantially constant first end section diameter;

a tip section having a diameter less than the first end section diameter;

a tapered section between the first end section and the tip section;

a second end section of a substantially constant second end section diameter detachably connected to a distal end of the tip section, the second end section diameter being greater than the diameter of the tip section and the first end section diameter;

wherein the second end section is configured to center the tip section as the corewire is passed through an extrusion apparatus and the second end section is configured to be detached from the corewire so as to define the tip section as a distal tip of the corewire;

feeding a first end of the corewire into an extrusion device;

translating the corewire through the extrusion device; and extruding an extrusion jacket onto an outer surface of the corewire as the corewire is translated through the extrusion device, the step of extruding including the step of centering the corewire in the extrusion device so that the extrusion jacket is concentric with the corewire.

5. The method of manufacturing of claim 4, wherein the step of centering the corewire comprises drawing the second end section through the extrusion device so that the second end section engages an opening in the extrusion device.

6. The method of manufacturing of claim 5, wherein the centering step results in a concentric extrusion jacket being extruded on the tip section.

7. The method of manufacturing of claim 6, further comprising the step of separating the second end section from the tip section after the extruding step.

8. The method of manufacturing of claim 7, further comprising, after the separating step, the step of providing a closed tip on the distalmost portion of the tip section of the extruded corewire.

9. A discrete length corewire to be used in manufacturing a guidewire, comprising:

a main shaft section of a substantially constant diameter;

a tip section having a substantially constant diameter less than the diameter of the main shaft section;

a tapered section between the main shaft section and the tip section, a first end of the tapered section having a diameter equal to the diameter of the main shaft section, a second end of the tapered section having a diameter equal to the diameter of the tip section;

an end section at an end of the tip section opposite the tapered section, the end section having a diameter greater than the diameter of the main shaft section;

wherein the end section is configured to center the tip section as the corewire is passed through an extrusion apparatus and the end section is configured to be removed from the corewire so as to define the tip section as a distal tip of the corewire; and a concentric jacket of extrusion material extruded onto an outer surface of the tip section;

wherein an outer diameter of the jacket is the same as or greater than the diameter of the end section.

10. A corewire of claim 9, wherein the tip section includes a predetermined bend.

11. A corewire of claim 9, wherein the end section includes a substantially constant diameter.

* * * * *